US007940296B2

(12) United States Patent
Ogino et al.

(10) Patent No.: US 7,940,296 B2
(45) Date of Patent: May 10, 2011

(54) IMAGE CAPTURING UNIT FOR ENDOSCOPE

(75) Inventors: Takayuki Ogino, Saitama (JP);
Kazuyuki Yamamoto, Saitama (JP);
Akihiro Ito, Saitama (JP); Seiichiro Okamura, Ibaraki (JP); Tomokazu Yamashita, Ibaraki (JP)

(73) Assignee: Hoya Corporation, Tokyo (JP)

( * ) Notice: Subject to any disclaimer, the term of this patent is extended or adjusted under 35 U.S.C. 154(b) by 1312 days.

(21) Appl. No.: 11/427,821

(22) Filed: Jun. 30, 2006

(65) Prior Publication Data
US 2007/0004965 A1 Jan. 4, 2007

(30) Foreign Application Priority Data

Jul. 1, 2005 (JP) ................................ 2005-193227
Jul. 6, 2005 (JP) ................................ 2005-197037

(51) Int. Cl.
*H04N 7/18* (2006.01)
(52) U.S. Cl. .......................................... 348/65; 348/76
(58) Field of Classification Search ............... 348/65–76
See application file for complete search history.

(56) References Cited

U.S. PATENT DOCUMENTS 6,390,972 B1 * 5/2002 Speier et al. .................. 600/112
6,933,962 B2    8/2005 Yamamoto

FOREIGN PATENT DOCUMENTS

| JP | 4-37053 | 2/1992 |
| JP | 9-192093 | 7/1997 |
| JP | 2003-100920 | 3/1998 |
| JP | 10-248803 | 9/1998 |
| JP | 11-290269 | 10/1999 |
| JP | 2000-60796 | 2/2000 |
| JP | 2001-311879 | 11/2001 |
| JP | 2002-291693 | 10/2002 |
| JP | 10-074865 | 4/2003 |
| JP | 2003-230532 | 8/2003 |

OTHER PUBLICATIONS

English language Abstract of JP 2003-100920.
English language Abstract of JP 10-074865.
U.S. Appl. No. 11/427,812 to Ogino et al., filed Jun. 30, 2006.
U.S. Appl. No. 11/456,253 to Ogino et al., filed Jul. 10, 2006.
U.S. Appl. No. 11/456,281 to Yamamoto et al., filed Jul. 10, 2006.
U.S. Appl. No. 11/456,288 to Yamamoto et al., filed Jul. 10, 2006.
Japanese Office Action that issued with respect to Japanese Patent Application No. 2005-193227, mailed Oct. 28, 2010, along with an English language translation thereof.

* cited by examiner

*Primary Examiner* — Andy S Rao
(74) *Attorney, Agent, or Firm* — Greenblum & Bernstein, P.L.C.

(57) ABSTRACT

An image capturing unit for an electronic endoscope, including a solid-state image capturing element, a metallic housing member, which hermetically encloses a circumference of an insulated base and is arranged to cover a front-end portion of the insulated base, at least one connection land, which is connected to at least one signal conductor at a position in vicinity to a rear-end portion of the insulated base outside the housing member, and a conductive cylindrical shield, which surrounds the at least one connection land and the at least one signal conductor and is spaced from the at least one connection land and the at least one signal conductor in a radial direction, is provided. An outer periphery of the rear-end portion of the insulated base is formed to be smaller than the circumference of the insulated base enclosed by the housing member.

14 Claims, 8 Drawing Sheets

IMAGE CAPTURING UNIT FOR ENDOSCOPE

BACKGROUND OF THE INVENTION

The present invention relates to an image capturing unit, which is adapted to be built in a tip portion of an electronic endoscope.

Generally, an image capturing unit of an electronic endoscope includes a solid-state image capturing element, an electrically insulated base to support the image capturing element, and a metallic housing to airtightly enclose the image capturing element and the insulated base therein. The image capturing unit further includes a plurality of connection lands that are arranged in vicinity to a rear end of the insulated base outside the housing and are connected to signal conductors thereat. Examples of such an image capturing unit are disclosed in Japanese Patent Provisional Publications Nos. 2003-100920 and HEI 10-74865.

As an inserted portion of a tip of the endoscope is adapted to be inserted into live bodies, the image capturing unit of the endoscope is required to be downsized by tenths of a millimeter to a minimum extent, However, in the image capturing units disclosed in the above-referenced publications, in order to inhibit noises to signals from intruding from connecting points of the connection lands and the conductors, the rear-end portion of the image capturing unit is required to be shielded by a conductive cylinder, which is arranged to be spaced in a radial direction from the connection lands and the signal conductors.

Therefore, as shown in FIG. 10, a diameter of a cylindrical shield 92, which extends from a circumference of an insulated base 91, tends to be greater than a diameter of a housing 94 that surrounds a solid-state image capturing element 93, and the like. In such a configuration, as an entire image capturing unit becomes greater, it becomes difficult to use the image capturing unit in an endoscope with a considerably smaller diameter In exchange, other components of the image capturing unit, such as a light guide for illumination and channel tubes, are required to be downsized in diameters thereof. Therefore, functionalities of the endoscope may have been limited by the configuration.

SUMMARY OF THE INVENTION

In view of the foregoing drawbacks, the present invention is advantageous in that an image capturing unit for an electronic endoscope, in which a cylindrical shield to surround contact points of connection lands and signal conductors is configured to be smaller, is provided, whilst functionalities of the endoscope may be substantially achieved, According to an aspect of the present invention, there is provided an image capturing unit for an electronic endoscope, including a solid-state image capturing element, which is adapted to capture an image of an object, a metallic housing member, which is adapted to airtightly or hermetically enclose a circumference of an insulated base holding the image capturing element and is arranged to cover a front-end portion of the insulated base, at least one connection land, which is connected to at least one signal conductor at a position in vicinity to a rear-end portion of the insulated base outside the housing member, and a conductive cylindrical shield, which is arranged to surround the position where the at least one connection land and the at least one signal conductor are connected and is spaced from the at least one connection land and the at least one signal conductor in a radial direction. An outer periphery of the rear-end portion of the insulated base is formed to be smaller than the circumference of the insulated base enclosed by the housing member, so that an outer periphery of the cylindrical shield is smaller than an outer periphery of the housing member.

Optionally, the cylindrical shield and the housing member may be electrically connected with each other.

Optionally, the insulated base may be formed to include a shield receiving portion, to which a front-end portion of the cylindrical shield is fitted. The cylindrical shield may be correctly positioned when the front-end portion of the cylindrical shield is fitted to receiving portion.

Optionally, a shield receiving member, to which the front-end portion of the cylindrical shield is fitted, may be fixed to a rear-end portion of the housing member, so that the cylindrical shield is correctly positioned when the front-end portion of the cylindrical shield is fitted to the shield receiving member.

Optionally, a portion of the housing member may be bent toward an axis thereof to form the rear-end portion, and the shield receiving member may be fixed to a rear surface of the rear-end portion.

Optionally, the shield receiving member may be adhesively fixed to the housing member.

Optionally, the shield receiving member may be brazed to the housing member.

Optionally, the shield receiving member may have a form of a frame, of which cross-sectional shape is an approximate rectangle.

Optionally, the shield receiving member may be made of an electrically insulated material.

Optionally, an outer peripheral surface of the shield receiving member may be metalized.

DETAILED DESCRIPTION OF THE EMBODIMENTS

Hereinafter, referring to the accompanying drawings, an image capturing unit of an electronic endoscope according to illustrative embodiments of the invention will be described.

First Embodiment

Figure 1:
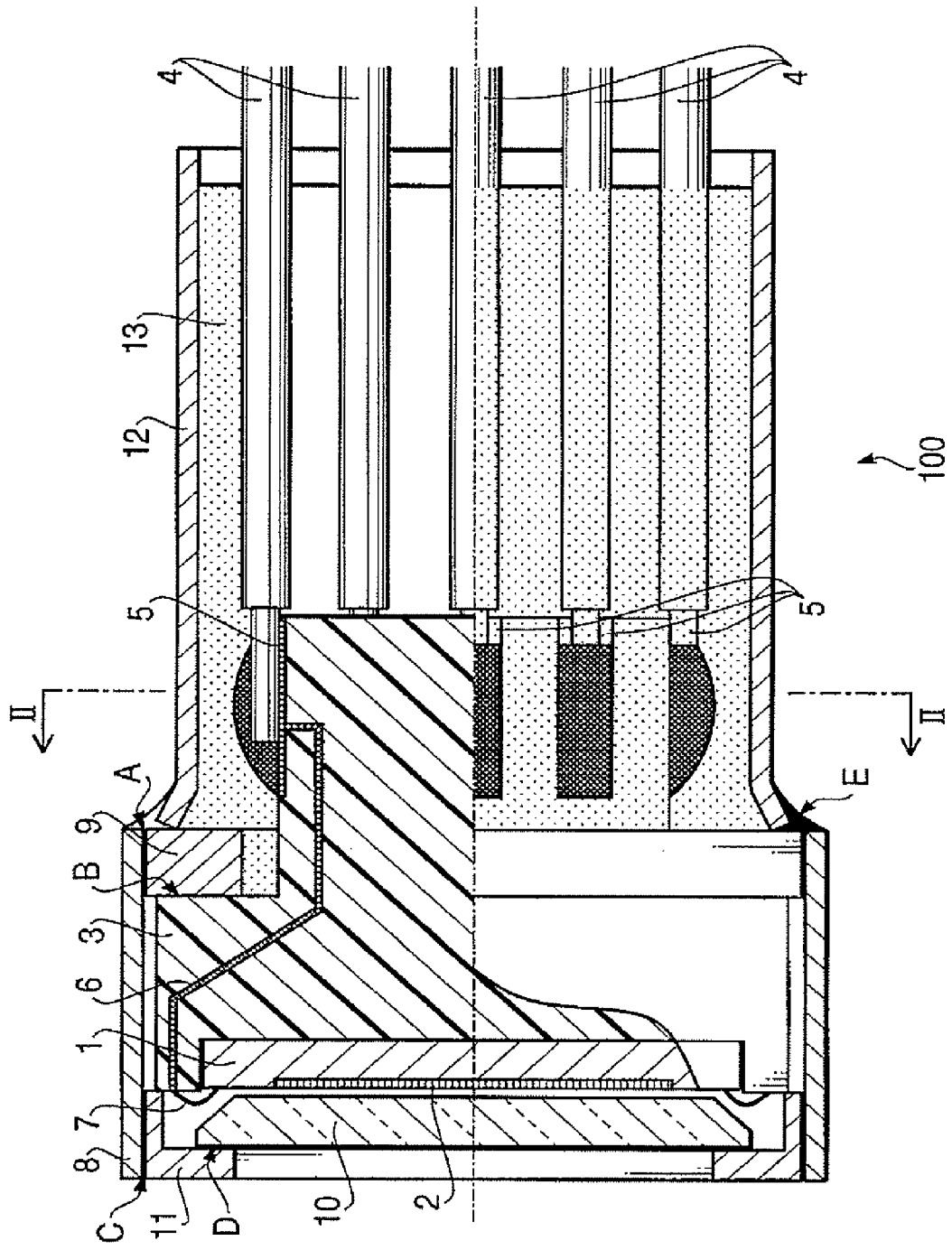
FIG. 1 is a cross-sectional side view of an image capturing unit for an electronic endoscope according to a first embodiment of the invention.

FIG. 1 is a cross-sectional side view of an image capturing unit 100 for an electronic endoscope according to a first embodiment of the invention. The image capturing unit 100 is provided at a tip of an inserted portion (not shown) of the endoscope, and includes a solid-state image capturing element 1, of which a front surface is formed to be an approximate rectangle. Further, an image capturing area 2, which is formed to be an approximate rectangle and substantially smaller than the image capturing element, is provided in a central portion of the image capturing element 1.

The image capturing element 1 is supported by an insulated block 3, which is made of an insulated material, such as ceramic. The insulated block 3 is formed to include a recessed portion at a front thereof, so that the image capturing element 1 is adhesively fixed therein.

On an outer surface of a rear portion of the insulated block 3, a plurality of connection lands 5 that are connected to signal conductors 4 are provided. The signal conductors 4 are arranged inside the inserted portion of the endoscope. Each of the connection lands 5 is connected to a rear end of one of conductors 5, which are buried in the insulated block 3 and extended in parallel with an axial direction of the inserted portion.

Further, in the image capturing unit 1, a plurality of bonding wires 7, which connect a circuit (not shown) of the image capturing element 1 with the conductors 6, are provided. The bonding wires 7 are arranged along two opposed edges of the image capturing element 1 to extend outwardly, so that each of the bonding wires 7 is connected to a front end of each of the conductors 6 that are exposed from two opposed edges of a front end of the insulated block 3. Each of the bonding wires 7 is curved toward a front of the image capturing element 1 as the bonding wire 6 extends from the front surface of the image capturing element 1.

The image capturing unit 100 further includes a housing 8, which contains the image capturing element therein. The housing 8 is made of one of metals, and has a shape of a rectangular cylinder that encircles by a front portion of the image capturing unit 100, so that vapor and the like should not enter the image capturing unit 100 during high-pressure and high-temperature steam sterilization.

The image capturing unit 100 includes an approximate rectangular rear frame 9, which is made of one of metals, and is arranged on an inner periphery at a rear portion of the housing 8, so that space between the housing 8 and the insulated block 3 is maintained. The rear frame 9 is airtight or hermetically sealed at an entire welding surface A to the housing 8, so that the rear frame 9 is assembled to be integral with the housing 8. Further, the rear frame 9 is airtight or hermetically sealed at an entire seal surface B to the insulated block 3 with a fixing method such as by welding, with an inorganic adhesive agent, for example.

The image capturing unit 100 includes an approximate rectangular front frame 9, which is made of one of metals, and is arranged on the inner periphery at a front portion of the housing 8. The front frame 11 is airtight or hermetically sealed at an entire welding surface C to the housing 8, whilst a rear end of the front frame 11 is in contact with the front end of the insulated block 3, so that the housing 8 is stabilized to the insulated block 3 through the front frame 11. Further, a transparent cover glass 10 to seal the front surface of the image capturing element 1 from exterior environment is provided. The cover glass 10 is airtight or hermetically sealed to a seal surface D of a front-most portion of the front frame 11.

The image capturing unit 100 further includes a cylindrical shield 12 to surround connecting portions of the signal conductors 4 and the connection lands 5, so that noises to signals through the signal conductors 4 and the connection lands 5 are inhibited from intruding. A front end of the cylindrical shield 12 is electrically connected to a rear end of the housing 8 (i.e., a soldered portion E is formed) by soldering.

Figure 2:
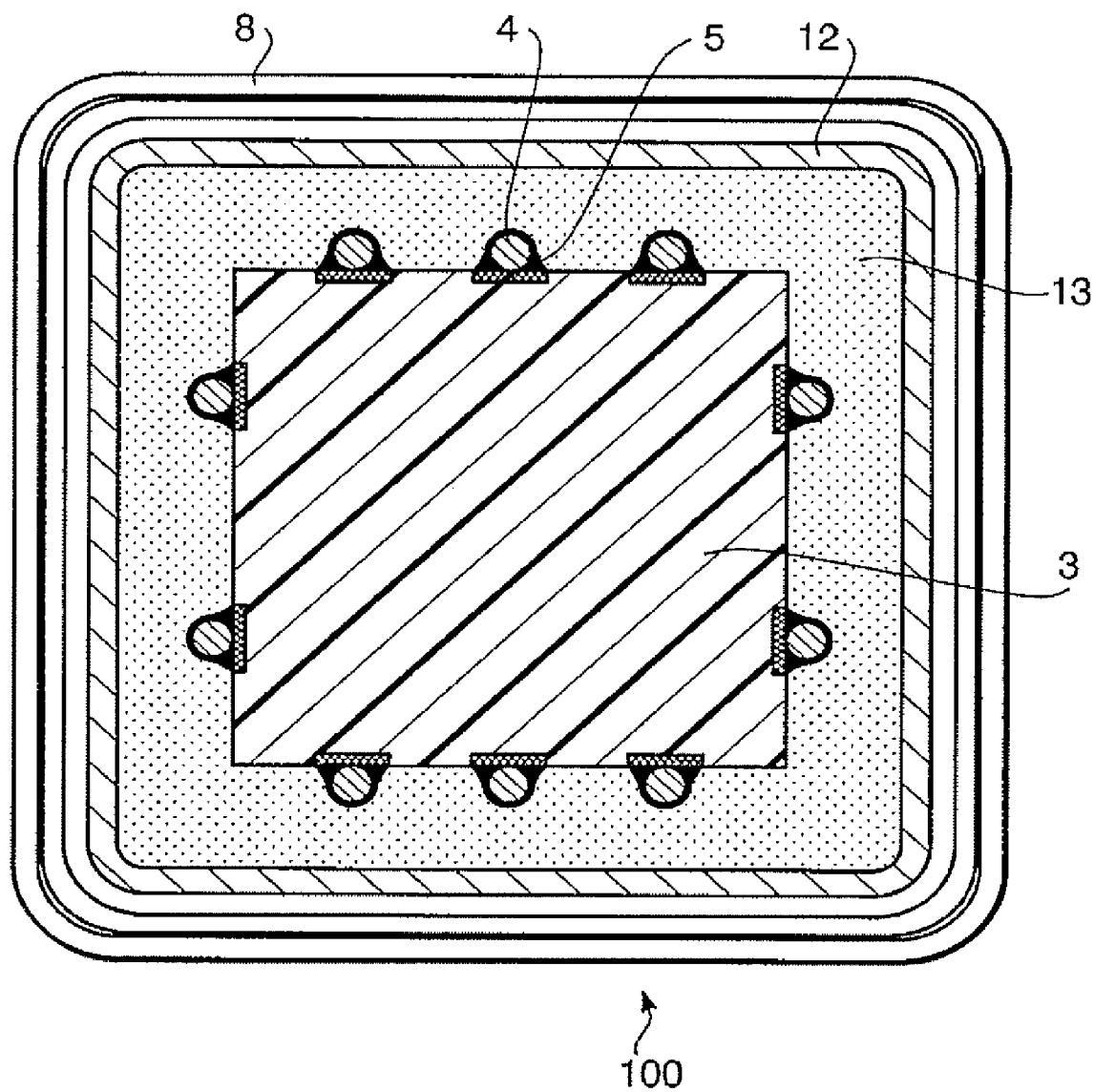
FIG. 2 is a plane view of the image capturing unit taken along a line II-II in FIG. 1 according to the first embodiment of the invention.

FIG. 2 is a plane view of the image capturing unit 100 taken along a line II-II in FIG. I according to the first embodiment of the invention. The cylindrical shield 12 is arranged to surround the connection lands 5 and the signal conductors 4 that are connected to the connection lands 5. As the cylindrical shield 12 is arranged, the cylindrical shield 12 is spaced from the connection lands 5 and the signal conductors 4 that are connected to the connection lands 5 in a radial direction, and a void space between the connection lands 5 and the signal conductors 4 and the cylindrical shield 14 is filled with a potting agent 13 such as an epoxy-based adhesive agent.

With the cylindrical shield 12 attached to the housing 8 by soldering, a diameter of the cylindrical shield 12 of the image capturing unit 100, is configured to be smaller than a diameter of a portion surrounded by the housing 8.

Therefore, a diameter of a portion of the image capturing unit 100, which extends from a connected portion between the cylindrical shield 12 and the housing 8, can be configured to be smaller, so that other components of the image capturing unit, such as a light guide for illumination and channel tubes, can be configured to have substantially larger diameters to provide substantially greater functionalities of the endoscope. Further, the image capturing unit 100 configured as above can be used in an endoscope with a small diameter.

Second Embodiment

Figure 3:
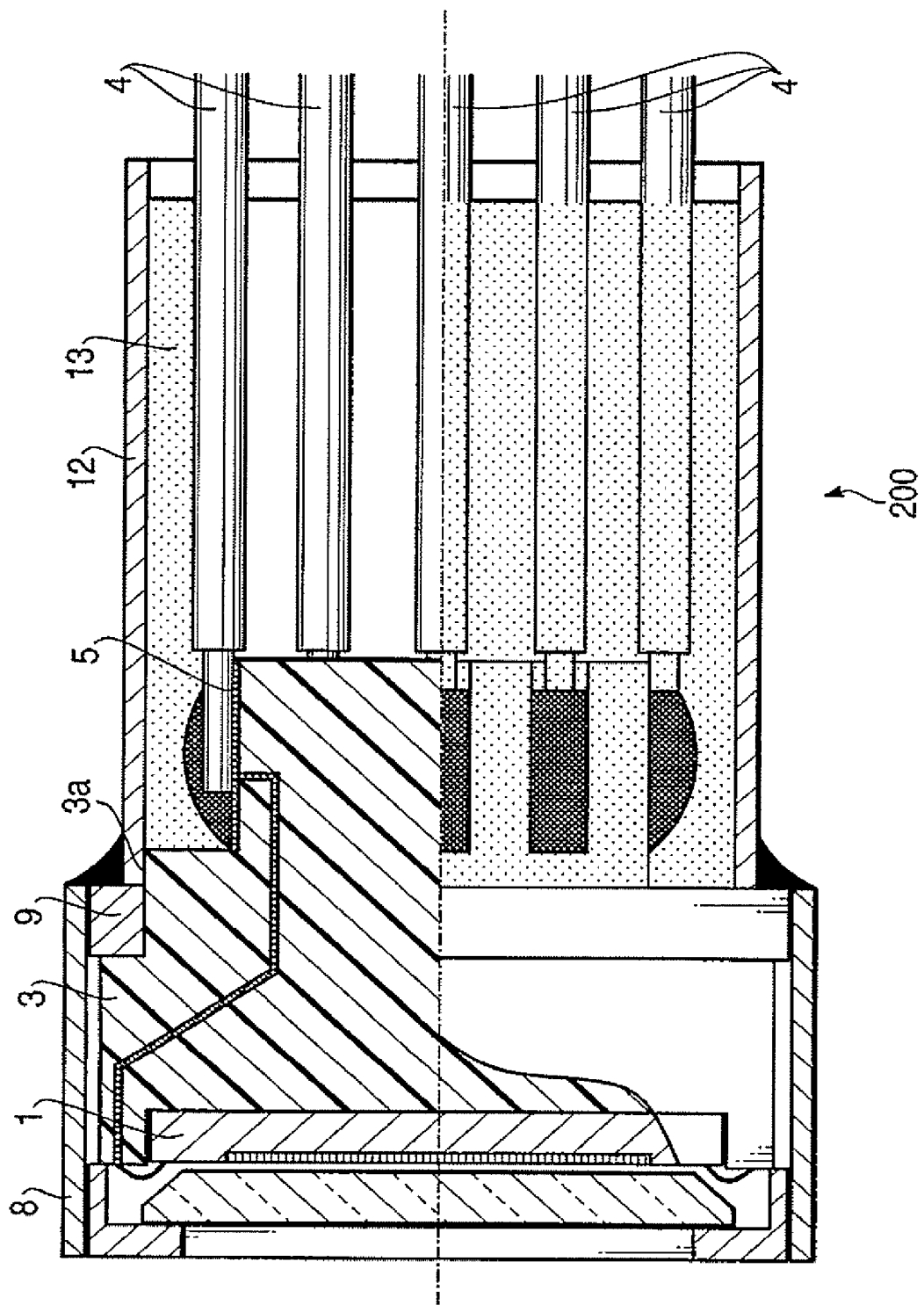
FIG. 3 is a cross-sectional side view of an image capturing unit for an electronic endoscope according to a second embodiment of the invention.

FIG. 3 is a cross-sectional side view of an image capturing unit 200 for an electronic endoscope according to a second embodiment of the invention. In the present and following embodiments, configurations corresponding to the configuration of the first embodiment is referred to by the identical reference numerals, and description of those is omitted.

In the present embodiment, the insulated block 3 is formed to have a shield receiving portion 3a on a circumference of the insulated block 3. The shield receiving portion 3a is formed to have a cross-sectional shape of an approximate rectangle, which is engaged with a front end of the cylindrical shield 12. With this configuration, the cylindrical shield 12 can be positioned easily and correctly in a radial direction and in a circumferential direction, as the image capturing unit 200 is assembled.

Third Embodiment

Figure 4:
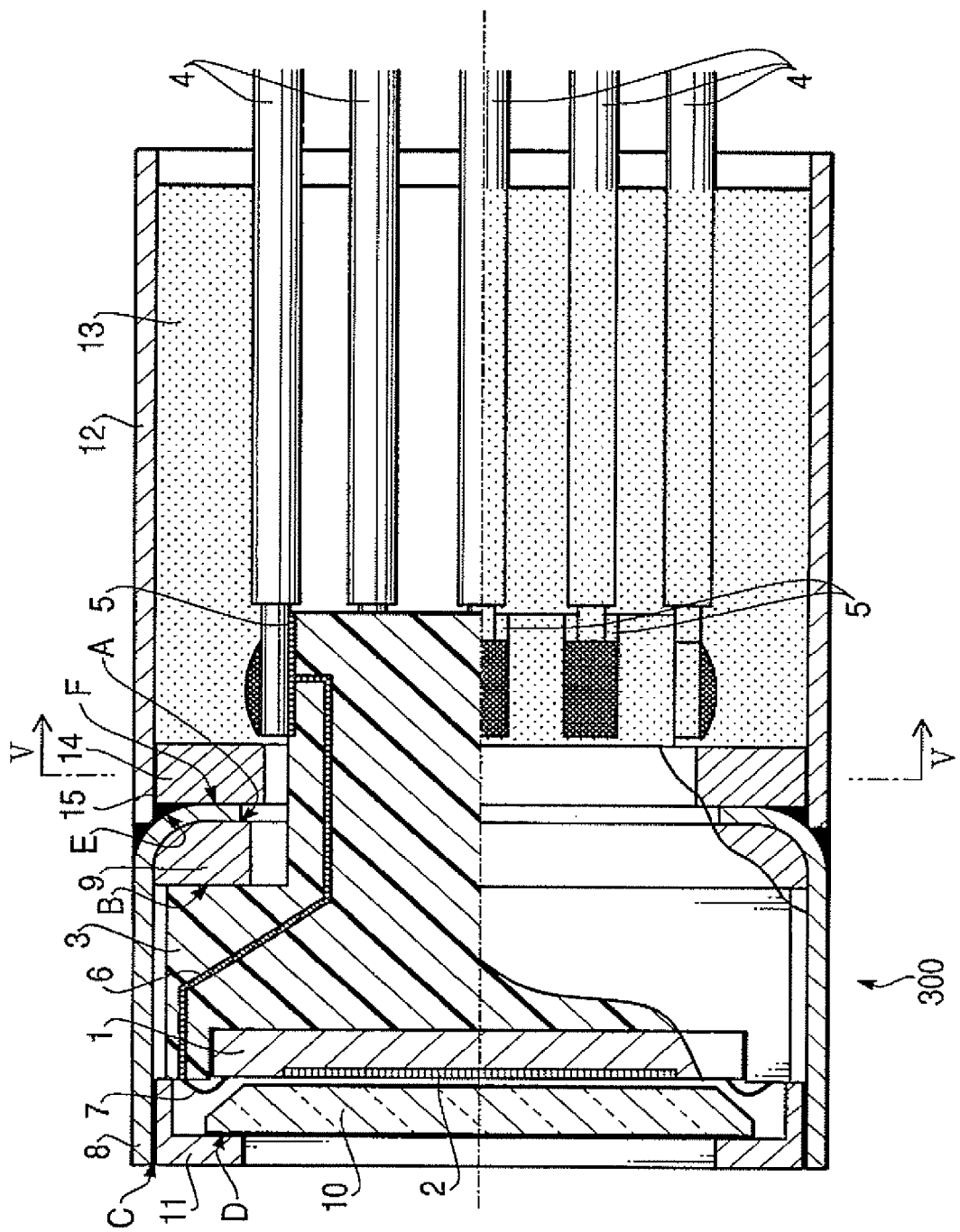
FIG. 4 is a cross-sectional side view of an image capturing unit for an electronic endoscope according to a third embodiment of the invention.
Figure 5:
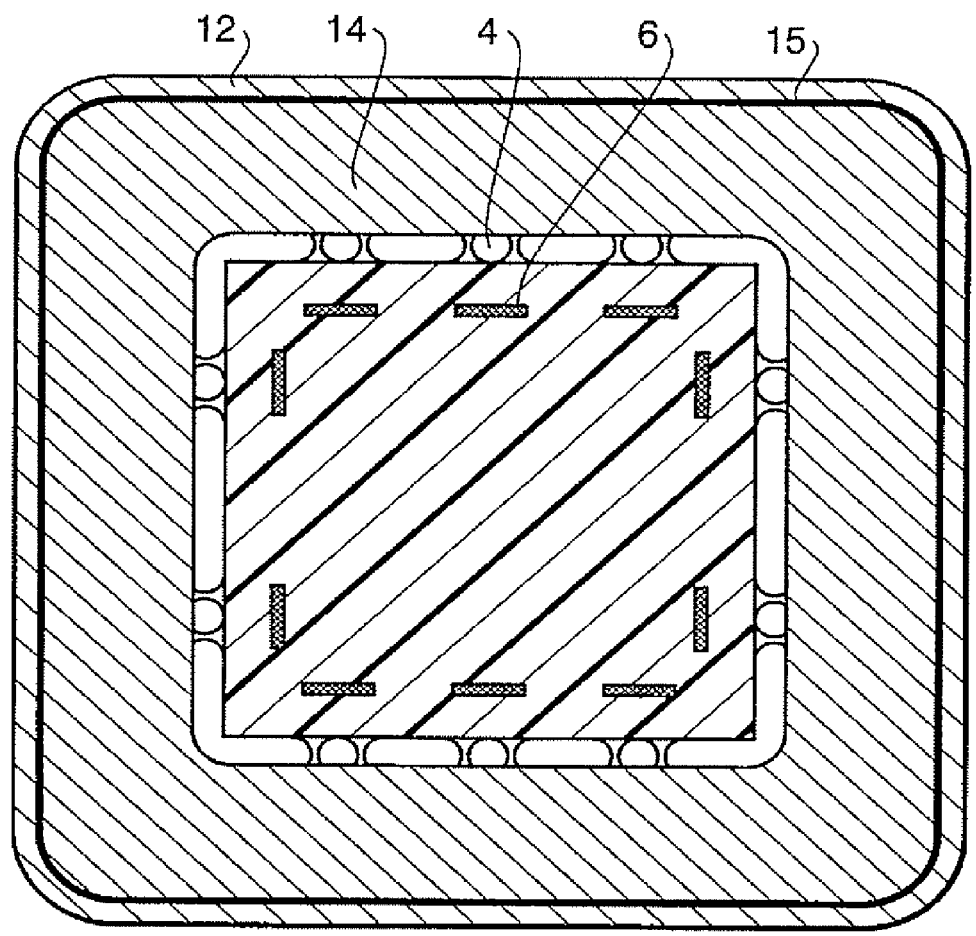
FIG. 5 is a plane view of the image capturing unit taken along a line V-V in FIG. 4 according to the third embodiment of the invention.
Figure 6:
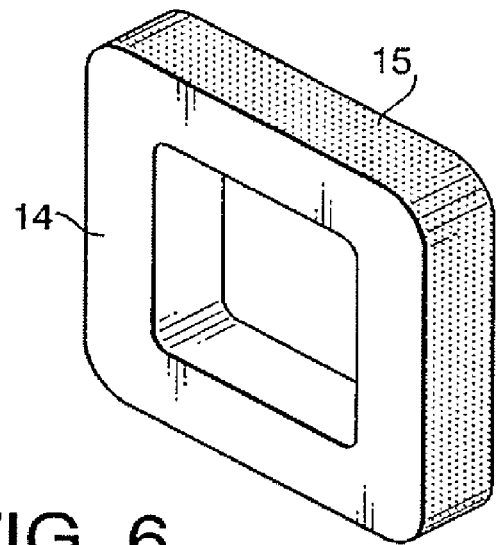
FIG. 6 is a perspective view of a shield receiving member of the image capturing unit according to the third embodiment of the invention.
Figure 7:
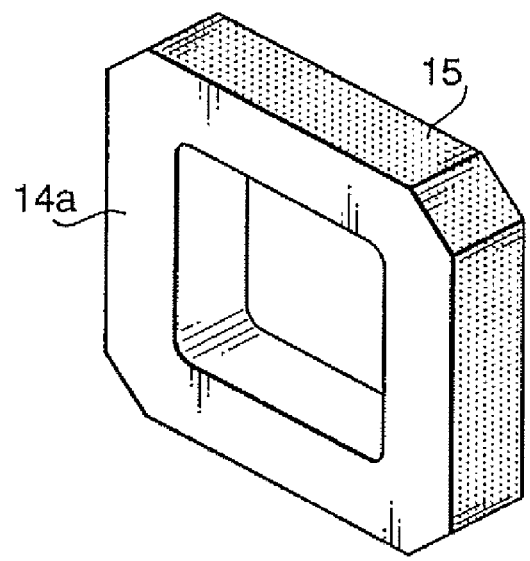
FIG. 7 is a perspective view of a variation of the shield receiving member of the image capturing unit according to the third embodiment of the invention.

FIG. 4 is a cross-sectional side view of an image capturing unit 300 for an electronic endoscope according to a third embodiment of the invention. FIG. 5 is a plane view of the image capturing unit taken along a line V-V in FIG. 4 according to the third embodiment of the invention. FIG. 6 is a perspective view of a shield receiving member 14 of the image capturing unit 300 according to the third embodiment of the invention. FIG. 7 is a perspective view of a variation of the shield receiving member 14a of the image capturing unit 300 according to the third embodiment of the invention.

In the present embodiment, the image capturing unit 300 is provided with the shield receiving member 14, which is fixed to a rear surface of the housing 8, and the cylindrical shield 12 is fixedly fitted to outer peripheral surfaces of the shield receiving member 14, The shield receiving member 14 is formed to be an approximate rectangular frame, which is substantially smaller than a diameter of the housing 8. The shield receiving member 14 is made with an insulated material, such as ceramic, so that the shield receiving member 14 can withstand voltage from the connection lands 5, which are arranged in vicinity to the shield receiving member 14, Outer peripheral surfaces (metalized surfaces 15) of the shield receiving member 14 is metalized, so that the metalized surfaces 15 can be easily soldered as the cylindrical shield 12 is attached to the shield receiving member 14. It should be noted that edges of the shield receiving member 14 may be beveled as shown in FIG. 7.

As the image capturing unit 300 is configured, the cylindrical shield 12 is required to be in an exactly correct position with respect to outer peripheral surfaces of the housing 8, so that outer peripheral surfaces of the cylindrical shield 12 do not protrude from the outer peripheral surfaces of the housing 8.

Figure 8:
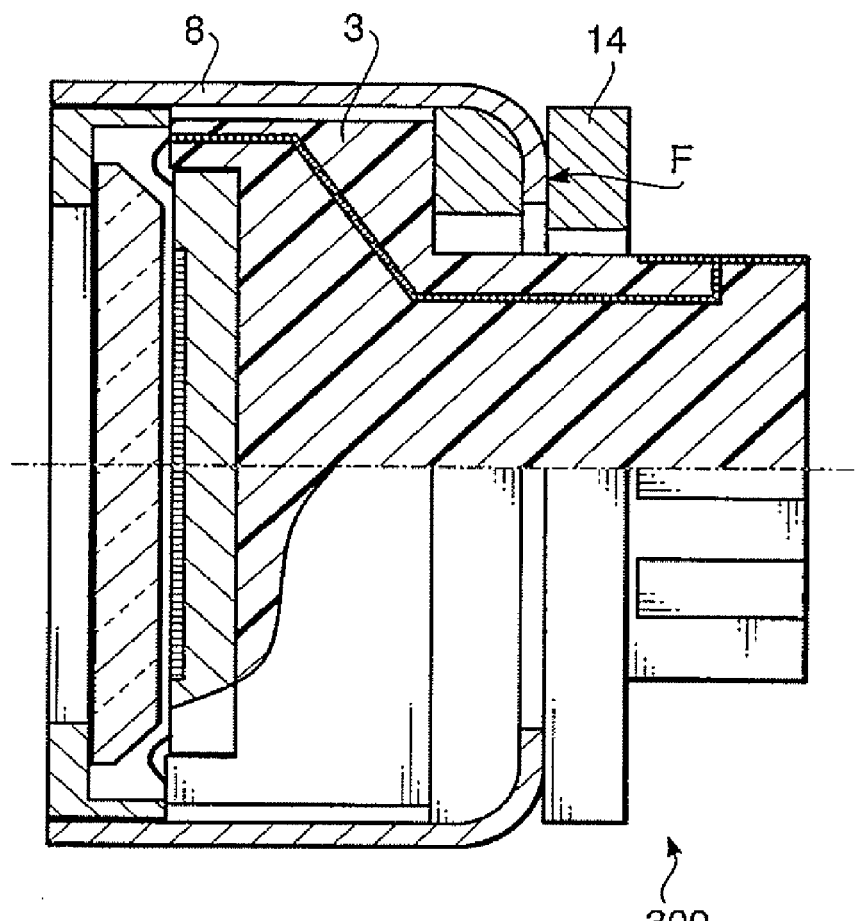
FIG. 8 is a cross-sectional side view of the image capturing unit before the cylindrical shield is installed according to the third embodiment of the invention.

FIG. 8 is a cross-sectional side view of the image capturing unit 300 before the cylindrical shield 12 is installed according to the third embodiment of the invention. The rear end portion of the housing 8 is bent toward an axis of the housing 8. The shield receiving member 14 is fixed to a rear surface (i.e., an adhered surface F) of the housing 8 in a correct position with respect to the housing 8 with heat-resistant adhesive agent, such as silicone-based adhesive agent and epoxy-based adhesive agent. The shield receiving member 14 may not necessarily be airtight or hermetically sealed to the adhered surface F.

In the present embodiment, it is preferred that the adhesive agent is resistant to heat ranging approximately from 300 to 350 degrees C., so that the adhesive agent should not be deteriorated by heat generated during a soldering work, that takes place in vicinity to the adhered surface F. As the shield receiving member 14 is adhered to the adhered surface F of the housing 8, positions of the outer peripheral surfaces of the shield receiving member 14 are accurately adjusted with respect to the outer peripheral surfaces of the housing 8 by using a tool (not shown) and the like.

Figure 9:
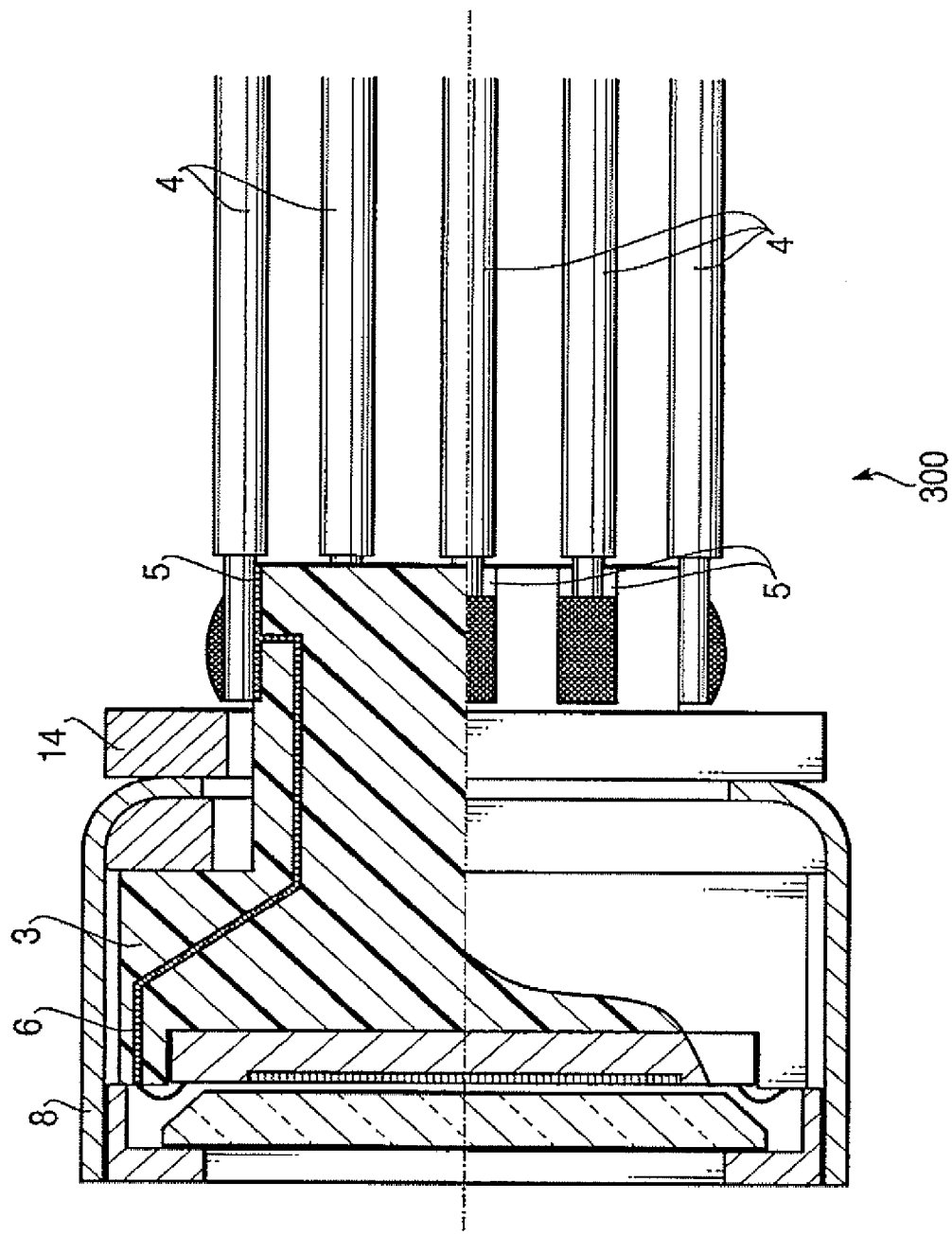
FIG. 9 is a cross-sectional side view of the image capturing unit before the cylindrical shield is installed according to the third embodiment of the invention.
Figure 10:
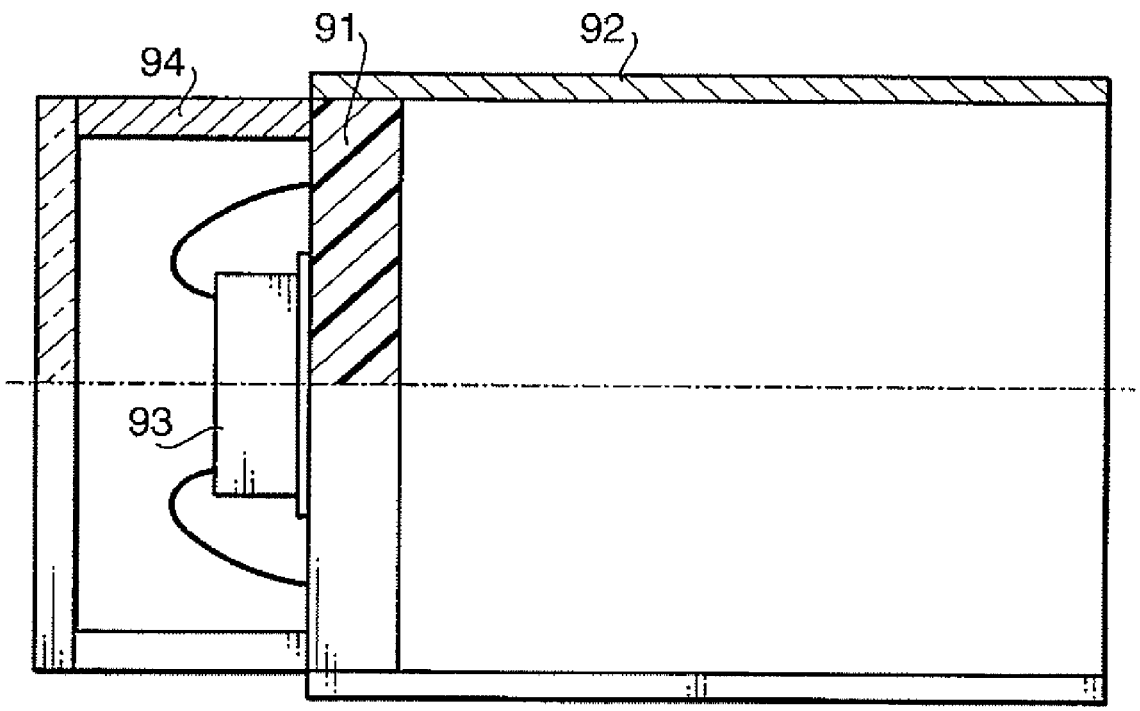
FIG. 10 is a cross-sectional side view of a conventional image capturing unit.

FIG. 9 is a cross-sectional side view of the image capturing unit 300 before the cylindrical shield 12 is installed according to the third embodiment of the invention. After the signal conductors 4 are soldered to the connection lands 5, as shown in FIG. 9, inner peripheral surfaces of a front end portion of the cylindrical shield 12 are closely fitted to the outer peripheral surfaces of the shield receiving member 14 (see FIG. 4). Thereafter, the front end portion of the cylindrical shield 12 along with the metalized surfaces 15 of the shield receiving member 14 is soldered to a soldered portion E of the housing 8. It should be noted that the soldering may be replaced with brazing with other conductive material.

With the above configuration, the cylindrical shield 12 can be attached to the housing 8 in the correct position with respect to the outer peripheral surfaces of the housing, whilst the outer peripheral surfaces of the cylindrical shield 12 do not protrude from the outer peripheral surfaces of the housing 8.

The present disclosure relates to the subject matter contained in Japanese Patent Applications Nos. P2005-193227, filed on Jul. 1, 2005 and P2005-197037, filed on Jul. 6, 2005, which are expressly incorporated herein by reference in their entireties.

What is claimed is:

1. An image capturing unit for an electronic endoscope, comprising:
    a solid-state image capturing element, which is adapted to capture an image of an object;
    a metallic housing member, which is adapted to hermetically enclose a circumference of an insulated base holding the image capturing element and is arranged to cover a front-end portion of the insulated base, the insulated base being in a shape of a block with a recessed portion at a front thereof;
    at least one connection land, which is connected to at least one signal conductor at a position in a vicinity to a rear-end portion of the insulated base outside the housing member; and
    a conductive cylindrical shield, which is arranged to surround the position where the at least one connection land and the at least one signal conductor are connected and is spaced from the at least one connection land and the at least one signal conductor in a radial direction,
    wherein an outer periphery of the rear-end portion of the insulated base is formed to be smaller than a circumference of the insulated base enclosed by the housing member, so that an outer periphery of the cylindrical shield is smaller than an outer periphery of the housing member.

2. The image capturing unit according to claim 1, wherein the cylindrical
    shield and the housing member are electrically connected with each other.

3. The image capturing unit according to claim 1,
    wherein the insulated base is formed to include a shield receiving portion, to which a front-end portion of the cylindrical shield is fitted, and
    wherein the cylindrical shield is correctly positioned when the front-end portion of the cylindrical shield is fitted to shield receiving portion.

4. The image capturing unit according to claim 1,
    wherein a shield receiving member, to which the front-end portion of the cylindrical shield is fitted, is fixed to a rear-end portion of the housing member, so that the cylindrical shield is correctly positioned when the front-end portion of the cylindrical shield is fitted to the shield receiving member.

5. The image capturing unit according to claim 4,
    wherein a portion of the housing member is bent toward an axis thereof to form the rear-end portion, and the shield receiving member is fixed to a rear surface of the rear-end portion.

6. The image capturing unit according to claim 4, wherein the shield receiving member is adhesively fixed to the housing member.

7. The image capturing unit according to claim 4, wherein the shield receiving member is brazed to the housing member.

8. The image capturing unit according to claim 4, wherein the shield receiving member has a form of a frame, of which a cross-sectional shape is an approximate rectangle.

9. The image capturing unit according to claim 4, wherein the cylindrical shield and the housing member are electrically connected with each other.

10. The image capturing unit according to claim 4, wherein the shield receiving member is made of an electrically insulated material.

11. The image capturing unit according to claim 10, wherein an outer peripheral surface of the shield receiving member is metalized.

12. An image capturing device for an electronic endoscope, comprising:
- an image capturer that captures an image of an object;
- a housing that hermetically encloses a circumference of an insulated base holding the image capturer, the insulated base being in a shape of a block with a recessed portion at a front thereof;
- a connection land connected to a signal conductor at a position in a vicinity to a rear-end portion of the insulated base outside the housing member; and
- a conductive cylindrical shield, that surrounds the position where the connection land and the signal conductor are connected and is spaced from the connection land and the signal conductor in a radial direction, an outer periphery of the rear-end portion of the insulated base being smaller than a circumference of the insulated base enclosed by the housing, so that an outer periphery of the cylindrical shield is smaller than an outer periphery of the housing.

13. The image capturer of claim 12, wherein the insulated base includes a shield receiver to which a front-end portion of the cylindrical shield is fitted, the cylindrical shield being correctly positioned when the front-end portion of the cylindrical shield is fitted to the shield receiver.

14. An image capturing device for an electronic endoscope, comprising:
- an image capturer that captures an image of an object;
- a housing that hermetically encloses a circumference of an insulated base holding the image capturer, the insulated base being block shaped with a recessed portion at a front thereof; and
- a cylindrical shield arranged around a signal conductor outside the housing, wherein an outer periphery of a rear-end portion of the insulated base is smaller than a circumference of the insulated base enclosed by the housing, so that an outer periphery of the cylindrical shield is smaller than an outer periphery of the housing.

* * * * *